United States Patent [19]

Keimel

[11] Patent Number: 4,553,547
[45] Date of Patent: * Nov. 19, 1985

[54] CARDIAC PACEMAKER SYNCHRONIZED PROGRAMMING

[75] Inventor: John G. Keimel, New Brighton, Minn.

[73] Assignee: Medtronic, Inc., Minneapolis, Minn.

[ * ] Notice: The portion of the term of this patent subsequent to May 7, 2002 has been disclaimed.

[21] Appl. No.: 634,236

[22] Filed: Jul. 25, 1984

Related U.S. Application Data

[62] Division of Ser. No. 371,335, Apr. 23, 1982, Pat. No. 4,515,160.

[51] Int. Cl.⁴ .............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 4,060,090 | 11/1977 | Lin et al. | 128/419 PG |
| 4,163,451 | 8/1979 | Lesnick et al. | 128/419 PG |
| 4,226,245 | 10/1980 | Bennett, Jr. | 128/419 PT |
| 4,228,803 | 10/1980 | Rickards | 128/419 PG |
| 4,230,120 | 10/1980 | McDonald | 128/419 PT |

FOREIGN PATENT DOCUMENTS

| | | | |
|---|---|---|---|
| 60117 | 9/1982 | European Pat. Off. | 128/419 PG |
| 163961 | 6/1980 | Netherlands . | |

Primary Examiner—William E. Kamm
Assistant Examiner—Mitchell J. Shein
Attorney, Agent, or Firm—Joseph F. Breimayer; John L. Rooney; Reed A. Duthler

[57] ABSTRACT

The programming of pulse intervals and the inhibition of the output of an implanted cardiac pacemaker are disclosed. The occurrence of either an output pulse from the implanted unit or of cardiac activity allows for synchronization of the programming unit with the implanted device so the external programmer can control the pulse timing sequence of the implanted unit. The implanted unit can be programmed after each pulse, or as required, to obtain a pulse sequence which may be used to provoke, or terminate, tachyarrhythmias, thus enabling non-invasive electrophysiologic studies, or therapeutic stimulation.

4 Claims, 3 Drawing Figures

CARDIAC PACEMAKER SYNCHRONIZED PROGRAMMING

This application is a divisional application of Ser. No. 371,335 filed Apr. 23, 1982 now U.S. Pat. No. 4,515,160 issued May 7, 1985 for "Cardiac Pacemaker Synchronized Programming" in the name of John G. Keimel.

BACKGROUND OF THE INVENTION

This invention relates to apparatus for controlling the time interval between consecutive output pulses of an implanted cardiac pacemaker, and thereby allowing non-invasive electrophysiologic studies, or therapeutic, cardiac stimulation for tachyarrhythmias.

The identification and diagnosis of cardiac tachyarrhythmias and the means of testing the efficacy of antiarrhythmia drug regimens are very often accomplished clinically through the use of electrophysiologic testing. This testing technique, which necessitates the introduction of single or multiple premature stimuli, or short bursts of rapid stimuli has, in the past, been primarily restricted to an invasive approach requiring catheterization.

An earlier attempt in U.S. Pat. No. 4,307,725, issued Dec. 29, 1981 to George E. Sowton et al discloses noninvasive electrophysiologic testing which uses an implanted pacemaker that required an external stimulator to produce short interval pulses on surface skin electrodes. These pulses were detected by the implanted device and used to trigger an output from the implanted device. This technique requires the implanted device to have a short refractory period (typically 180 ms or shorter). Using a short pacemaker refractory period, a normal pacemaker sensing circuit could inadvertently sense "T" or "R" waves, or electrode polarization, and thereby upset the desired stimulation sequence. In addition, when using this technique, the maximum delay between any two pulses is the escape interval of the pacemaker.

The Keller, et al U.S. Pat. No. 4,203,447 describes a technique in which data which has already been transmitted is transferred into permanent memory at the time of an output pulse.

The technique of the present invention allows for changing the internal program on successive pulses. For instance, if two rate programs are transmitted immediately after two successive output pulses, the results would be definite: The Spectrax SXT TM pulse generator manufactured by Medtronic, Inc., is an example of a buffered device which may be programmed in accordance with the present invention.

But, if the program transmissions are not synchronized with the output pulses, unexpected results could occur.

DESCRIPTION OF THE DRAWINGS

The present invention is described by reference to the drawings in which.

TECHNICAL DESCRIPTION OF THE INVENTION

The invention described herein overcomes the problems that existed with the prior art devices by transmitting the pulse interval data directly to the memory section of the implanted unit by means of a telemetry system. This data controls the escape time to the next output pulse. The implanted unit is not required to use the cardiac sensing amplifier to obtain the pulse interval data, and the refractory period can therefore be at a normal length, or the sense amplifier can be turned off completely. The pulse interval data does not trigger the implanted unit, as in the above-noted technique, but programs the timer of the implanted device.

Figure 1:
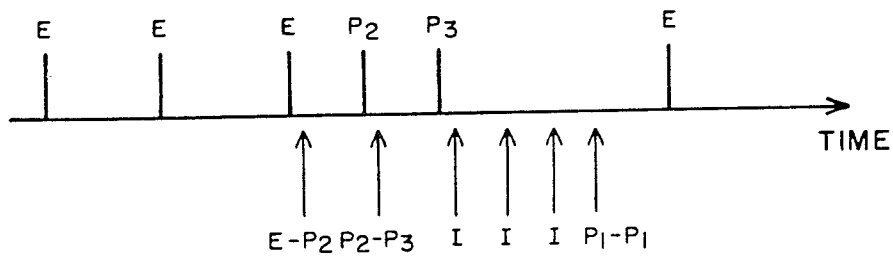
FIG. 1 is a timing chart which shows event and programming pulses associated with the present invention.

FIG. 1 illustrates a timing sequence of the external programming device with respect to the pacemaker events of the implanted unit. Pacemaker events (E) can be either output pulses or sensed cardiac activity which resets the timing circuitry of the implanted device. That is, if the sensed events occur prior to the end of the normal escape interval (P1-P1), E represents a sensed event. If no sensed event occurs prior to the end of the escape period, there is an output pulse, controlled by the user. The lower part of FIG. 1 represents the timing of the programmer transmissions which are synchronized with the pacemaker events. The actual programming sequence will vary, depending upon the implanted pacemaker, the number of intervals that need to be changed, and the length of any delay in the pacemaker sequence.

The first transmission in the example of FIG. 1 will program the implanted device to have an escape interval of a selected time E-P2. The second transmission, also synchronized to a pacemaker event, P2, again changes the escape interval of the implanted device to a time P2-P3. This process can be repeated for any number of pulses. In order to insert a delay in the pulsing sequence, inhibit transmissions (1) can be programmed, thus preventing the next output pulse. The last programming transmission restores the implanted device to the normal rhythm (escape interval P1-P1). The programming of premature pulses can only be accomplished while using the EKG cable which connects to the front of the programmer. The programmer also provides a timing signal from the expansion connector on the rear of the unit. This signal occurs following the fourth from the last S1 pulse prior to a premature pulse.

The premature pulse programming capabilities of the programmer are accomplished by the transmission of timed sequences of programming codes. The start of each transmission sequence is synchronized by pacemaker pulses detected by the EKG lead. The programming codes consist of pulse interval data or inhibit signals. The pulse interval data signals are "Temporary" codes from the Spectrax-SXT TM pulse generators. Inhibit codes are always "Temporary". Permanent programming remains in effect after the programming head (magnet) is removed from the vicinity of the pulse generator. Temporary programs will revert to the permanent program after the program head is removed.

The programmer of the present invention has been designed to program premature stimuli or controlled bursts of rapid stimulation with pulse intervals down to 180 milliseconds on the Spectrax-SX TM and Spectrax-SXT TM pulse generators manufactured by Medtronic, Inc. The sequence of programming codes will typically consists of one or more pulse interval codes which represent the desired premature or burst pulse interval. These will be followed by a number of inhibit codes, depending upon the selected delay value. The basic pacing rate (S1-S1 interval) is also reprogrammed near the end of the programming sequence.

The sequence of programming codes is synchronized to S1 pulses when programming premature pulses. The synchronization is accomplished by the detection of S1 pulses on the EKG lead connected to the front of the programmer. The programming of premature pulses therefore requires the placement of the EKG skin electrodes so as to allow detection of the pacing pulses. The programmer allows the selection of up to three premature stimuli which are synchronized to pacing pulses. Each of the premature stimuli intervals are adjustable from 180 to 500 msec. The programmer also allows the selection of the basic pacing interval (S1-S1) which is adjustable from 406 to 999 msec. The burst pulse interval adjustable from 180 to 500 msec., and the added delay following the premature pulses or burst of pulses is adjustable from 0 to 9 seconds.

Prior to the start of the programming transmission sequence, the implanted device is previously programmed to some normal cardiac pacing rate. The implanted device is capable of communicating the time at which the beginning of each cycle occurs, that is the time of either a output pulse event or a sense event. This means of communicating the occurrence of an event could be accomplished by a number of techniques which may include: (1) sensing the pulses from skin electrodes while the device is programmed to VVT or AAT mode; (2) sensing the pulses from skin electrodes while the implanted device is programmed to VOO or AOO mode; (3) receiving telemetry information from the implanted device which identifies the occurrence of an event; and (4) while in VOO, AOO, VVT, or AAT mode, detection of the radio frequency noise associated with the pulse of current through the patient. The external device is able to detect or receive this informtion by means of skin electrodes, a telemetry antenna, or a noise pickup antenna. The signal can then be amplified by the appropriate circuitry and detected or decoded by circuitry appropriate for the particular signal being received. The event timing information is made available to the control unit.

Prior to actually changing any escape interval, the user enters the pulse interval information (P1-P1, P1-P2, P2-P3, ... P[N-1]-P[N], and delay time) for each change in interval through a keyboard or other input device. The display allows the user to review the pulse sequence selected. At the time of a command from the user on the keyboard, the control unit awaits a selected number of cardiac events, then loads a buffer register with the telemetry code required to program the particular implanted device to the next interval selected. The coded information is transferred to the implanted device along with other programming codes required by the particular pacemaker.

The control unit may then either await the next pacemaker event from the detector or actually time the interval until the next expected event. The output buffer is then reloaded with the coding information of the next selected pulse interval and is transmitted to the implanted device. This can be repeated until the pulse interval is to return to a normal rhythm or until a delay is required. At that time, the controller will load the output buffer with coded information which, when received by the implanted device, will inhibit the next pacemaker output or return the device to the normal rhythm. If a delay is required, the inhibit transmission will occur at regular intervals, each of which inhibits the next escape output pulse, and will be repeated a number of times as required by the selected delay period.

The programmer has application in non-invasive electrophysiologic studies where electrical stimulation of the heart is used for:
refractory measurements
initiation of reentrant tachyarrhythmias
termination of reentrant tachyarrhythmias
sinus mode overdrive
location of accessory pathways
testing the intactness of the conduction system.

The programming head must be held in position over the pulse generator for the entire programming sequence. Failure to allow programming of the S1-S1 interval, which occurs near the end of the programming sequence may inadvertently leave the device programmed to a rate corresponding to one of the premature or burst pulse intervals. If this occurs, the desired rate may be obtained by programming rate or S1-S1 interval.

Figure 2:
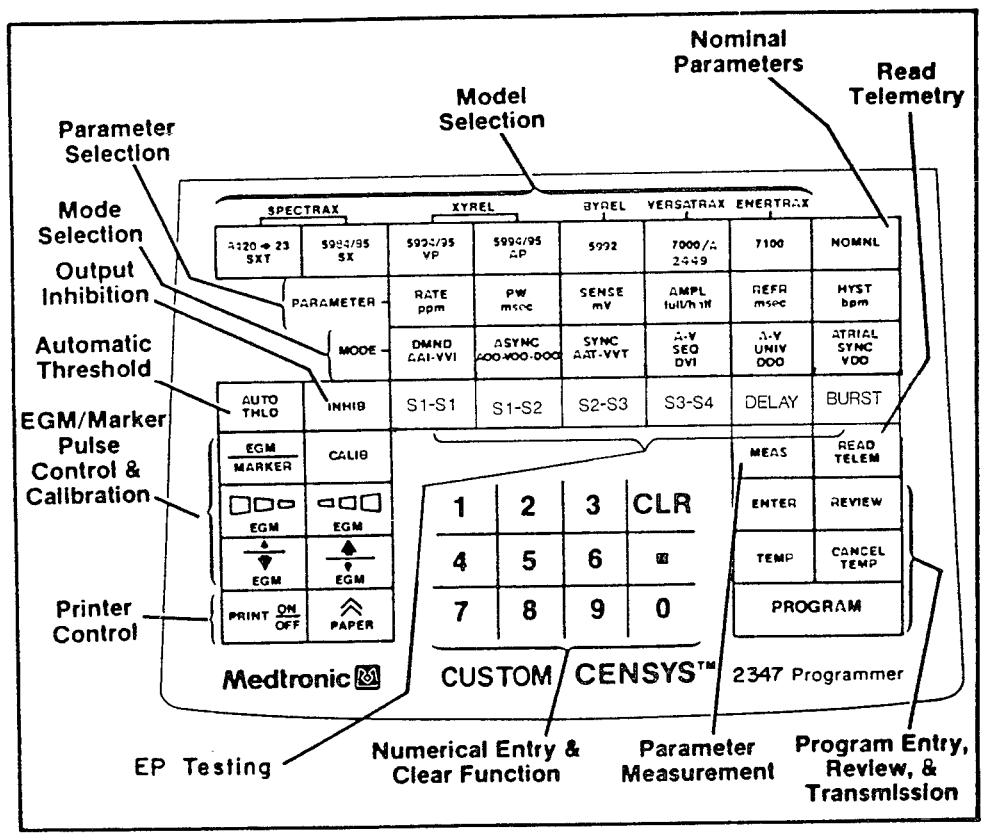
FIG. 2 is a plan view of the keyboard of the programmer of the present invention.
Figure 3:
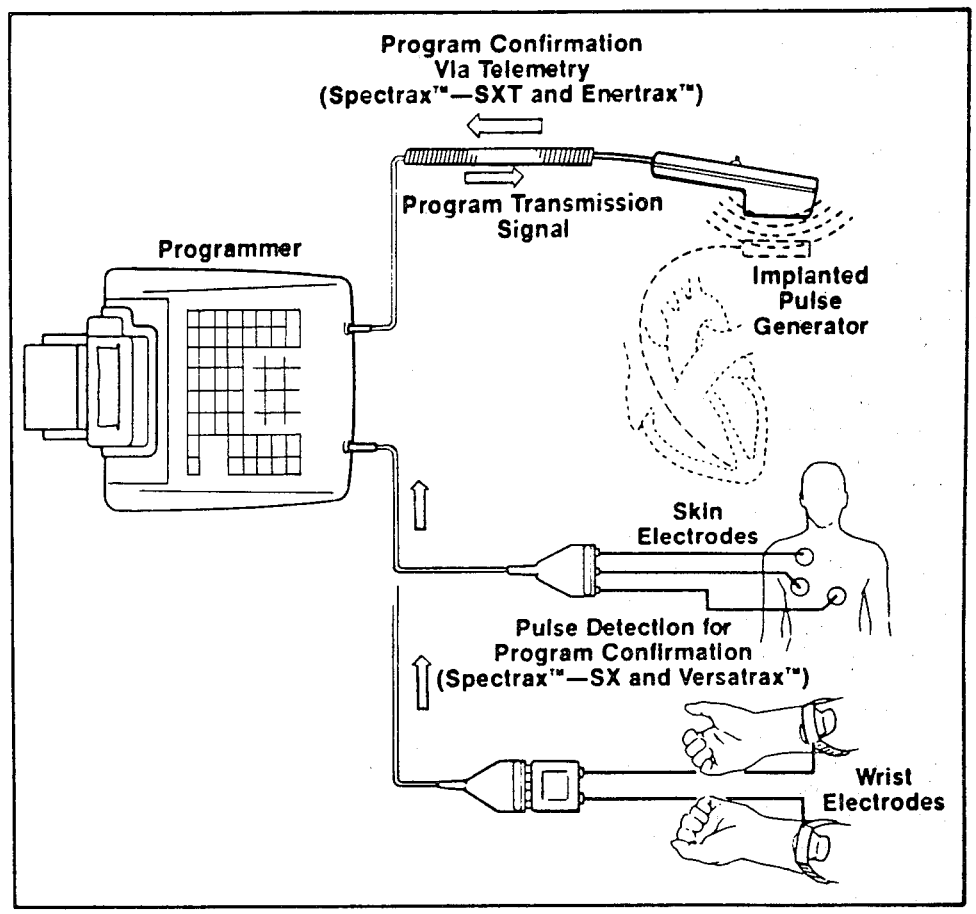
FIG. 3 is an overall view of the programming system employed to implement the present invention.

The programmer of the present invention has all the keys and features of the Model 9701A programmer manufactured by Medtronic, Inc. except that it cannot be used with the Byrel ® Model 5992 pulse generator, also manufactured by Medtronic, Inc. In addition to the standard features of the Model 9701A programmer, the programmer of the present invention has six additional keys which allow the programming of premature or burst pulses. After selection of the MODEL key which identifies the pulse generator model being programmed (see FIGS. 2 and 3).

The six keys are:

S1-S1. Pressing this key allows the user to adjust or program the S1-S1 pulse interval. When the device is powered-on, the initial or default value of the S1-S1 interval is 601 msec. This value is adjustable from 406 to 999 msec. by pressing the numerical keys and then pressing ENTER. The value entered will be automatically rounded to the nearest programmable value based upon the resolution of the implanted device (7.8 msec). Whenever a S1-S1 interval is displayed, it may be programmed by holding the programming head over the implanted pulse generator, waiting three seconds, and pressing PROGRAM. The display will indicate DONE when the transmission is complete (no automatic confirmation of the programming is available). The S1-S1 interval should be programmed prior to programming a premature pulse sequence.

S1-S2. Pressing the S1-S1 key also allows the user to adjust the number of S1 pulses which will precede the premature stimuli. The "count" value will have an initial value of 8 after the device is powered-on. It can be adjusted from 4 to 99 by pressing the numerical keys and then pressing ENTER. The current value of the count is displayed preceding "S1-S1". Pressing this key allows the user to review the current value, to adjust the S1-S2 interval, or to program a single premature pulse, S2. When the programmer is powered-on, the S1-S2 interval is 398 msec. This value is adjustable from 180 to 500 msec. by pressing the numerical keys and then pressing ENTER. The value entered will be automatically rounded to the nearest programmable value (7.8 msec resolution). The value may also be decremeted in multiples of 7.8 msec by simply entering the factor (between 1 and 9). For example, if the current value is 398 msec., pressing "2" and ENTER will result in a new value of 382 msec.

A single premature pulse (S2) may be programmed whenever the display indicates a valid S1-S2 interval value and pacing pulses can be detected on the surface EKG electrodes. The S1-S2 interval should be programmed and the programming head kept held in position prior to the premature pulse interval programming. Programming the premature pulse sequence occurs after pressing PROGRAM. The programming head must be held in position over the pulse generator until the display indicates "DONE." The programming sequence will be started after the required number of S1 pulses have been detected.

DELAY. Following the transmission of the premature pulse interval data, the programmer will transmit inhibit signals for the length of time selected by DELAY and will program the pulse generator to the selected S1-S1 interval data. The programming sequence can be placed in a loop where the displayed premature pulse interval is automatically decremented by a selected value on each loop. That is, after the selected DELAY has occured on the first loop, the S1 pulses are counted for the next premature pulse sequence (see FIG. 1). This is selected by pressing the decrement factor of 7.8 msec., "0" (for loop), and then ENTER.

This loop mode is indicated by a display of the decrement factor in front of the premature pulse interval. When the loop mode is set, the programming sequence is started by pressing PROGRAM. As previously mentioned, the programming head must be held in position over the pulse generator until the loop mode is terminated. During the initial loop, the displayed premature interval remains unchanged, but on each following loop the displayed value will be decremented by the selected factor. (The display is updated following the fourth from the last S1 pulse preceding a premature pulse). A stimulation program may be terminated at any time by pressing the CLEAR key.

This key allows the selection or review of the delay time. When the programmmer is powered-on, the delay time is set to 0 seconds. The delay time is adjustable from 0 to 9 seconds by pressing the desired number key and then pressing ENTER. This delay time represents the length of time the implanted pulse generator will be inhibited following the last premature pulse or burst pulse. The actual time from the last premature pulse or burst pulse to the first S1 pulse will be the delay time selected, plus up to two S1-S1 intervals.

S2-S3. Pressing this key allows the user to adjust the S2-S3 pulse interval value, to review the current value, or to program two premature pulses, S2 and S3. Value adjustment and the programming procedure is similar to that described for the S1-S2 key. When the loop mode is selected only the S2-S3 interval will be decremented. The S1-S2 pulse interval will be the previous value selected using key S1-S2.

S3-S4. Pressing this key allows the user to adjust the S3-S4 pulse interval value, to review the S3-S4 value, or to program three premature pulses , S2, S3 and S4. Value adjustment and the programming procedure is similar to that described for the S1-S2 key. When the loop mode is selected, only the S3-S4 interval will be decremented. The S1-S2 pulse interval and the S2-S3 pulse interval will be the current value associated with the respective keys.

BURST. This key allows the user to review the current value of the burst pulse interval, to select a new value, or to actually program a burst of rapid stimulation. When the programmer is turned on, the burst pulse interval is set to 398 msec. This pulse interval is adjustable from 180 to 500 msec. by pressing the numerical key and then pressing ENTER. A burst of rapid stimulation can be programmed by holding the programming head over the implanted pulse generator, waiting three seconds, and pressing PROGRAM. The rapid stimulation will continue until the PROGRAM key is released. Following the rapid stimulation burst the implanted pulse generator will be inhibited for the selected delay time and will be programmed to the selected S1-S1 interval. A signal is also provided on the expansion connector, located on the rear of the unit, which will identify when the fourth from the last S1 pulse preceding a premature pulse has occured.

The implementation of the present invention is shown in the acccompanying program files, which are written in PLM-80 programming language which is compatible with Intel TM microprocessors. The programmer that ultilizes the program of the present invention is generally shown in U.S. Pat. Nos. 4,208,008, issued June 17, 1980 and 4,236,522 issued Dec. 2, 1980, both of which are assigned to the assignee of the present invention, and these patents are hereby incorporated by reference herein.

What is claimed is:

1. A method of controlling the output pulse intervals of the pulses emitted by an implantable programmable cardiac pulse generator means which normally operates under the control of a main program transmitted from a control location to said pulse generator means comprising the steps of:
  (a) transmitting secondary pulse interval program information from a control location to said pulse generator means which specifies the interval between at least one cardiac depolarization event and an ensuing output pulse;
  (b) sensing the occurrence of cardiac depolarization events at said control location;
  (c) interrupting the control of said pulse interval established by said main program of said pulse generator means upon the satisfaction of predetermined criteria by said sensed cardiac depolarization event;
  (d) utilizing repeated transmissions of said secondary pulse interval program information to provide the specified interval between said cardiac events and said ensuing pulses before said ensuing pulses are specified to occur; and,
  (e) re-establishing control of the operation of said pulse generator by said main program upon utilization of said secondary pulse interval program information by retransmitting said main program to said pulse generator.

2. A method as claimed in claim 1 comprising the additional steps of:
  (f) storing pulse sequence information that specifies the occurrence of a programmed pulse sequence that is generated by said pulse generator means;
  (g) sensing the occurrence of said programmed pulse sequence;
  (h) terminating the further generation of any other pulses of said pulse sequence upon said sensing of said pulse sequence;

(i) sensing the occurrence of a sequence of cardiac depolarization events following said sensing of said pulse sequence;

(j) initiating the generation of said programmed pulse sequence upon said sensing of said event sequence; and, (k) repeating steps (g) through (j) in a cyclic manner.

3. A method as claimed in claim 2 where said output pulse and said next following output pulse are part of said pulse sequence.

4. A method as claimed in claim 3 comprising the additional steps of:

storing inhibit information; and, utilizing said inhibit information to delay the repetition of said steps (i) and (j) each time said steps (g) and (h) are completed.

* * * * *